(12) United States Patent
Diehl et al.

(10) Patent No.: US 11,311,689 B2
(45) Date of Patent: Apr. 26, 2022

(54) BREATHING APPARATUS COMPRISING A DIFFERENTIAL PRESSURE SENSOR

(71) Applicant: WEINMANN EMERGENCY MEDICAL TECHNOLOGY GMBH + CO. KG, Hamburg (DE)

(72) Inventors: Marcus Diehl, Hamburg (DE); Stefan Hein, Hamburg (DE); Matthias Pulla, Hamburg (DE); Frank Herrmann, Barmstedt (DE)

(73) Assignee: WEINMANN EMERGENCY MEDICAL TECHNOLOGY GMBH & CO. KG, Hamburg (DE)

( * ) Notice: Subject to any disclaimer, the term of this patent is extended or adjusted under 35 U.S.C. 154(b) by 380 days.

(21) Appl. No.: 16/485,559

(22) PCT Filed: Feb. 16, 2018

(86) PCT No.: PCT/DE2018/000043
§ 371 (c)(1),
(2) Date: Aug. 13, 2019

(87) PCT Pub. No.: WO2018/149436
PCT Pub. Date: Aug. 23, 2018

(65) Prior Publication Data
US 2019/0366025 A1    Dec. 5, 2019

(30) Foreign Application Priority Data
Feb. 20, 2017    (DE) ..................... 10 2017 001 558.9

(51) Int. Cl.
*A61M 16/00* (2006.01)
*F04D 25/08* (2006.01)
(Continued)

(52) U.S. Cl.
CPC ......... *A61M 16/0066* (2013.01); *A61B 5/087* (2013.01); *A61M 16/0003* (2014.02);
(Continued)

(58) Field of Classification Search
CPC .............. A61M 16/00; A61M 16/0057; A61M 16/0066; A61M 16/0069;
(Continued)

(56) References Cited

U.S. PATENT DOCUMENTS 7,975,688 B1    7/2011  Truitt
2009/0246013 A1*  10/2009  Kenyon ................. F04D 29/441
                                                    415/208.2
(Continued)

FOREIGN PATENT DOCUMENTS

WO    2007024955 A2    3/2007
WO    2013133889 A1    9/2013
WO    WO-2016121448 A1 *  8/2016  ............. F04D 29/58

OTHER PUBLICATIONS

Machine translation of WO-2016121448-A1.*

*Primary Examiner* — Joseph D. Boecker
(74) *Attorney, Agent, or Firm* — Lucas & Mercanti, LLP; Klaus P. Stoffel

(57) ABSTRACT

A method and apparatus for breathing, in which a blower is mounted in a specific part made of silicone, which reduces blower immissions and emissions. Moreover, the conducting structure influences the flow of the respiratory gas in order to reduce interference when measuring the volumetric flow.

9 Claims, 6 Drawing Sheets

(51) Int. Cl.
- *F04D 29/056* (2006.01)
- *F04D 29/58* (2006.01)
- *A61B 5/087* (2006.01)
- *G01F 1/42* (2006.01)
- *F04D 17/16* (2006.01)
- *F04D 29/66* (2006.01)

(52) U.S. Cl.
CPC ............ *F04D 25/08* (2013.01); *F04D 29/056* (2013.01); *F04D 29/5826* (2013.01); *G01F 1/42* (2013.01); *A61M 2016/0027* (2013.01); *A61M 2205/3334* (2013.01); *A61M 2205/3372* (2013.01); *A61M 2205/42* (2013.01); *F04D 17/16* (2013.01); *F04D 29/668* (2013.01)

(58) Field of Classification Search
CPC ...... A61M 2205/3372; A61M 2205/36; A61M 2205/3606; A62B 18/006; A62B 18/045; A42B 3/28; F04D 29/056; F04D 29/5826; F04D 29/668; F04D 13/0633; F04D 25/062; F04D 25/08

See application file for complete search history.

(56) References Cited

U.S. PATENT DOCUMENTS

| | | | |
|---|---|---|---|
| 2012/0138058 A1* | 6/2012 | Fu | A61M 16/0633 128/204.23 |
| 2012/0152255 A1* | 6/2012 | Barlow | A61M 16/0066 128/205.25 |
| 2016/0138611 A1* | 5/2016 | Teramoto | F04D 29/668 128/204.18 |
| 2021/0404484 A1* | 12/2021 | Hägele | A61C 19/007 |

* cited by examiner

BREATHING APPARATUS COMPRISING A DIFFERENTIAL PRESSURE SENSOR

CROSS-REFERENCE TO RELATED APPLICATIONS

The present application is a 371 of International application PCT/DE2018 000043, filed Feb. 16, 2018, which claims priority of DE 10 2017 001 558.9, filed Feb. 20, 2017, the priority of these applications is hereby claimed and these applications are incorporated herein by reference.

BACKGROUND OF THE INVENTION

The invention relates to a device for respiration and a method for respiration. In particular, an application in the case of mobile emergency respiration devices is intended.

In the case of inadequate or absent independent breathing of an oxygen-requiring living being, the breathing work has to be carried out as a life-supporting measure by a third party either manually, for example by mouth-to-mouth respiration or with the aid of respiration bags, or by machine using a respiration device to ensure the gas exchange in the lungs and thus supply the organs with oxygen and also exhale $CO_2$.

One reliable method according to the prior art is machine respiration, which is part of the medical equipment of rescue workers and clinical personnel in the form of respiration devices.

Modern respiration devices and methods offer important functions for effective and simultaneously gentle respiration of patients using volume and/or pressure monitoring. An excessively high pressure can damage the lung tissue, while an excessively low respiration volume results in an undersupply of oxygen. The frequency of the respiration is also precisely adaptable to international guidelines using known respiration devices, which guidelines are to ensure effective respiration, also in the case of resuscitation measures.

In the case of mobile respiration devices, they are frequently subjected to impacts during use, for example, caused by rough parking, loading, or due to falls. The forces suddenly occurring in the event of impacts can also occur at critical locations inside a respiration device, which can possibly be damaged by these suddenly occurring forces. One critical location is, for example, the fan, in particular the bearing and the shaft of the fan, which can be damaged by lateral forces.

Furthermore, the fans of known devices for respiration frequently generate structure-borne noise and, in conjunction with the guide structures of the devices for respiration, turbulent flows, which can result in noise emission and vibrations of the device for respiration, on the one hand, and can negatively influence the frequently used volume flow measurement of the respiratory gas, on the other hand.

According to the prior art, the cooling air of mobile respiration devices is only blown out in order to dissipate heat during the respiration of a patient. In some cases, this has the result that the respiration device is not sufficiently cooled in a switched-on state and damage to components results or at least the service life of individual components is shortened.

SUMMARY OF THE INVENTION

One object of the invention is to make the fan of the device for respiration less sensitive with respect to impacts.

This object is achieved according to the invention in that the fan motor is supported on at least one special part made of silicone.

A further object of the invention is to reduce the interfering influence of the fan on the volume flow measurement of the device for respiration.

This object is achieved according to the invention in that the fan is supported on at least one special part made of silicone, and in that the flow of the air in the overpressure range is calmed by a positive guide.

A further object of the invention is to permanently cool the device for respiration in a switched-on state by blowing out the cooling air.

This object is achieved according to the invention in that the fan also runs in a switched-on state of the device for respiration, in which no respiration takes place.

An embodiment according to the invention of a device for respiration comprises at least one fan, via which the ambient air can be suctioned via a filter into a fan chamber inside the housing of the device for respiration. The fan is implemented as a fan module, which comprises, in addition to a fan wheel, at least one heat sink and a fan motor. The fan module is supported according to the invention using at least one silicone part at least at two ends, so that emissions and immissions, in particular within the meaning of structure-borne noise and/or vibrations and impacts, from or on, respectively, the fan module can be damped.

In one advantageous embodiment of the invention, the fan module is supported with the aid of two silicone parts in the housing, which are designed as a first bearing element and a second bearing element.

The region of the silicone part supporting the fan module in the region of the heat sink or the corresponding bearing element, respectively, comprises at least one outflow opening and is furthermore designed as a guide structure for air in such a way that the air pressed by the fan into the fan chamber can be positively guided via the heat sink to implement an effective heat exchange.

The cooling air can be blown via a cooling screen out of the housing, which comprises at least one outlet. The volume flow of the exiting cooling air is settable by the diameter of the outlet or the outlets in conjunction with the internal pressure in the region of the cooling screen and the restoring force of a check valve arranged in the region of the outlet.

In one advantageous embodiment, the device according to the invention for respiration comprises a cooling screen having two outlets formed as cylindrical tubes, which have a diameter of 1.5 mm to 3.5 mm and using which a cooling airflow between 25 L/minute and 75 L/minute is implementable.

In one particularly advantageous embodiment of the invention, the device according to the invention for respiration comprises a cooling screen having two outlets formed as cylindrical tubes, which have a diameter of 2 mm to 3 mm and using which a cooling airflow of approximately 50 L/minute is implementable.

In one advantageous embodiment of a method according to the invention for respiration, the ambient air flows via a hygiene filter into the device. From there, it enters the intake region of the fan chamber, is suctioned in by the fan and is blown via an opening in the fan cap into the pressure region of the fan chamber. From here, the air, positively guided by the bearing element of the fan at least partially manufactured from silicone, flows via the cooling ribs of the heat sink of the fan toward the cooling valve. The silicone part fulfills a double function in this case: on the one hand, it is used as a damper against shock and vibration, or dropping of the device, and on the other hand, it is used as a positive guide for the air, which transports away the heat of the fan via the cooling ribs of the heat sink.

In one particularly advantageous embodiment of the method according to the invention for respiration, the heat absorbed by the heat sink of the fan is permanently dissipated outward, even if respiratory gas dispensing to a patient is absent.

Furthermore, in one advantageous embodiment of a device according to the invention for respiration, the bearing element implementing the guide structure for the air in the overpressure region is designed in such a way that the airflow is calmed, so that an interfering influence on a volume flow measurement carried out in the region of the device according to the invention is reduced. This is implemented according to the invention, for example, in that the bearing element has multiple equivalently formed outflow openings, which calm the airflow in conjunction with the structure of the heat sink, in the region of the heat sink of the fan.

In the region of the heat sink, the silicone part or the corresponding bearing element is formed like an overcoat in one advantageous embodiment of the invention, so that it can be slipped at least in regions over the heat sink of the fan similarly to a sleeve and radially peripherally encloses it.

In addition to the damped supporting of the fan, the silicone part implements or the bearing elements implement, in one advantageous embodiment of the invention, sealing off of the various pressure regions in the surroundings of the fan from one another. The sealing off is implemented by the structure of the silicone part or the bearing elements in conjunction with the structure of the housing enclosing the fan, for example, in such a way that the silicone part or the bearing element in the region of the intake opening of the fan seals this off from a first overpressure region in the region of the heat sink of the fan by a structure formed like a tongue and groove.

BRIEF DESCRIPTION OF THE DRAWING

Various exemplary embodiments and designs of the invention are shown in the following figures. In the figures

DETAILED DESCRIPTION OF THE INVENTION

Figure 1:
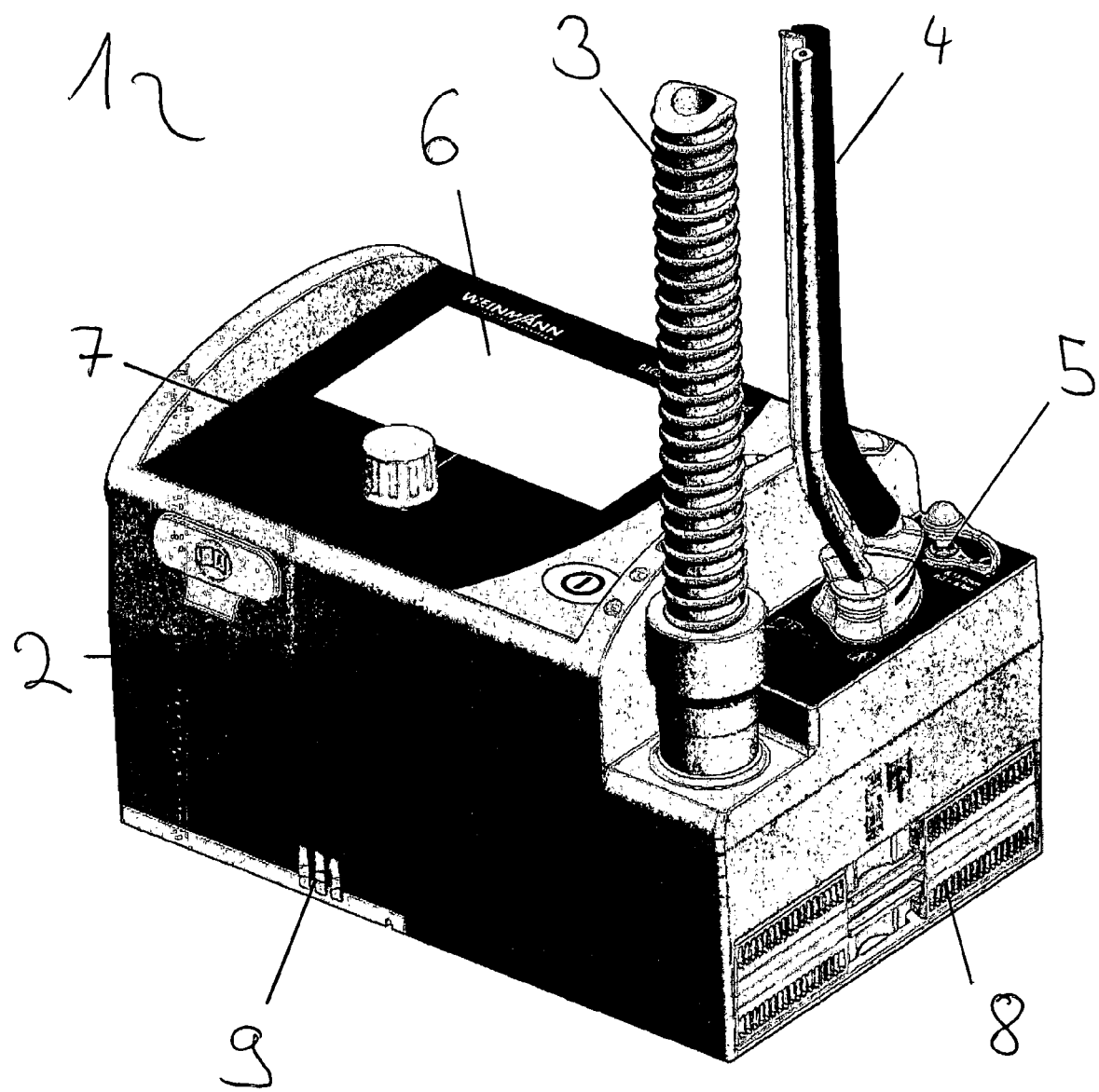
FIG. 1: shows a perspective illustration of a device according to the invention for respiration.

FIG. 1 shows a perspective illustration of a device according to the invention for respiration (1). The device for respiration (1) Is integrated in a housing (2), which is manufactured from an impact-resistant plastic in one advantageous embodiment. Connection devices are arranged in the right region of the housing upper side of the device for respiration (1).

In the illustrated embodiment, the device for respiration (1) comprises a respiration hose (3), an oxygen hose, and a measuring tube system (4) and a pressure fitting (5) for an oxygen source.

As user interfaces, the device for respiration (1) comprises a display screen (6) and an operating element (7) designed as a rotating knob.

An air inlet (8) is arranged on the right side of the housing (2) of the device for respiration (1) In a lower region and an air outlet (9) is arranged on the front side of the housing (2) in a lower region.

Figure 2:
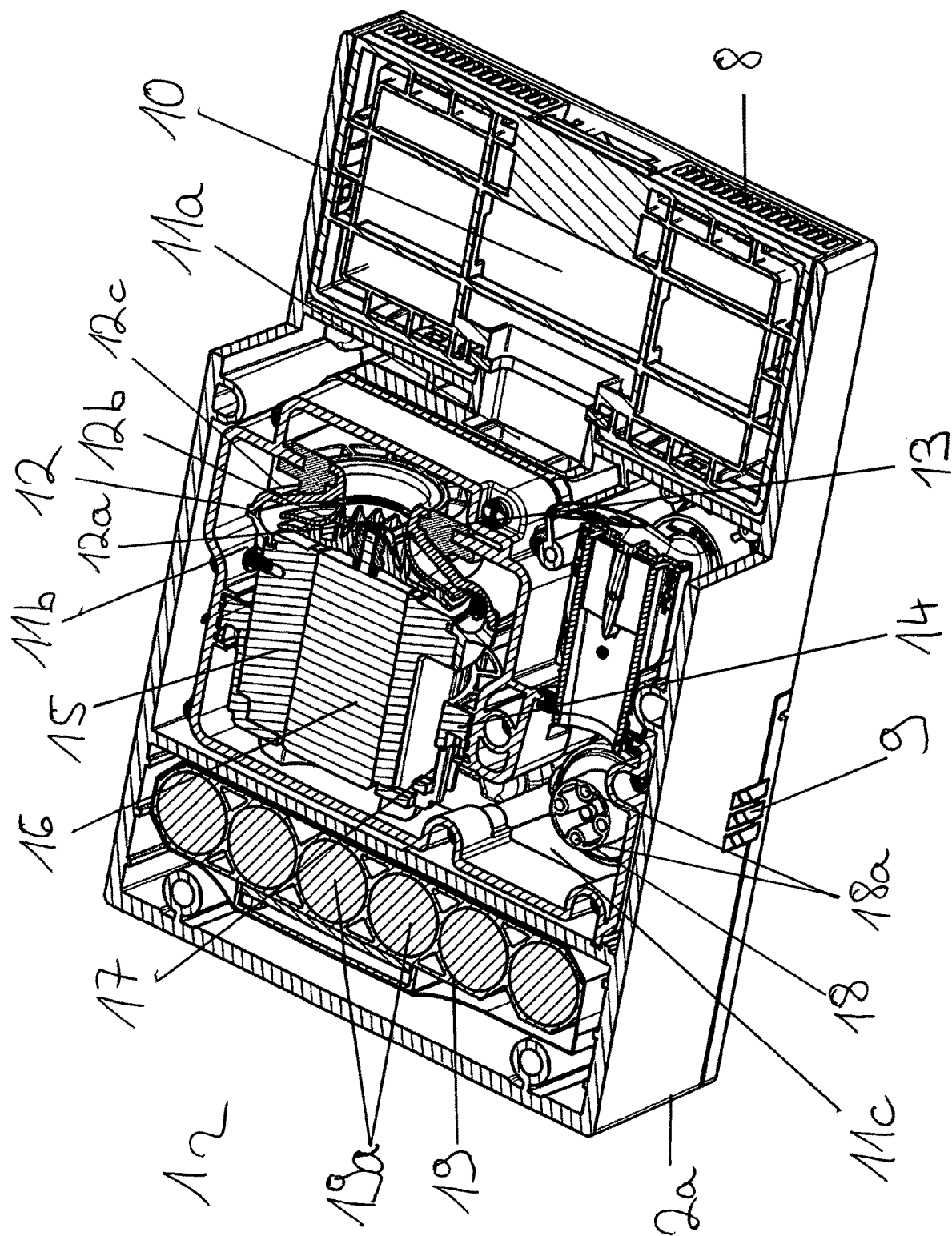
FIG. 2: shows a horizontal section through a device according to the invention for respiration, comprising a shock-absorbing fan support.

A perspective view in multiple horizontal sections of a device according to the invention for respiration (1) is shown in FIG. 2. The air inlet (8) can be seen on the right side in a housing lower part (2*a*) of the device for respiration (1). From the air inlet (8), the ambient air can be suctioned in by a fan (12) through a filter (10), particularly advantageously designed as a hygiene filter, via an intake region (11).

The fan (12) is advantageously designed as a radial fan and comprises a fan wheel (12*a*), a fan shaft (12*b*), and a fan cap (12*c*), which encloses the fan wheel (12*a*) and the fan shaft (12*b*).

On the side of the intake region (1*a*), the fan (12) is supported in a first bearing element (13), which is at least partially manufactured from silicone according to the invention. Moreover, the first bearing element (13) implements a seal between intake region (11*a*) and a first overpressure region (11*b*), in which the air enters through an opening in the fan cap (12*c*).

This first overpressure region (11*b*) is spatially delimited by a housing structure and a second bearing element (14) and encloses the heat sink (15) of the fan (12). A fan motor (16), which drives the fan shaft (12*b*), is integrated in the middle of the heat sink (15). The second bearing element (14) supports the heat sink (15) and the fan (12) connected thereto in the housing (2) and is at least partially manufactured from silicone according to the invention, so that impacts and structure-borne noise are damped. In addition, an outflow opening (17) is arranged in the second bearing element (14) in such a way that in addition to the supporting of the fan (12), a positive guide of the air is implemented, so that the air flows inside the first overpressure region (11*b*) via the cooling ribs of the heat sink (15), before it flows through the outflow opening (17) in the second bearing element (14) Into a second overpressure region (11*c*).

A cooling screen (18), which comprises two cylindrical tubes (18*a*), which lead via a check valve to the air outlet (9) of the device for respiration (1), is arranged in the region of the second overpressure region (11*c*).

An energy storage element (19), which is designed as an accumulator and has six cells (19*a*) in the embodiment shown, is arranged in the left region of the housing lower part (2*a*).

Figure 3:
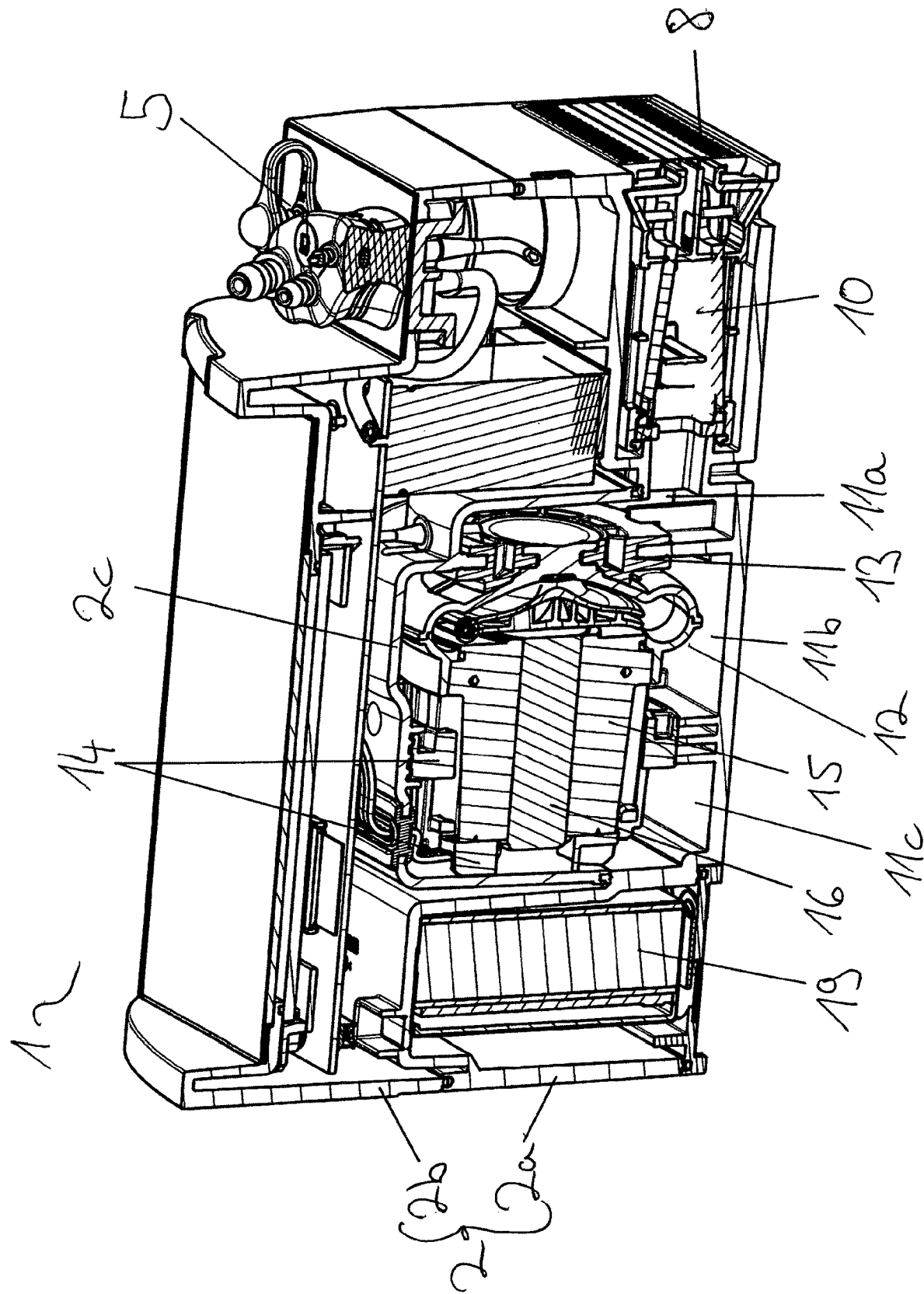
FIG. 3: shows a vertical section through a device according to the invention for respiration, comprising a shock-absorbing fan support.

FIG. 3 shows a perspective view of a vertical section through a device according to the invention for respiration (1). In addition, in particular the various pressure regions (11) In the region of the fan (12) can be seen in FIG. 3.

The intake region (11*a*) is located in the region adjoining the fan (12) on the right and is delimited and sealed off from the first overpressure region (11*b*) with the aid of the first bearing element (13). The air enters the first overpressure region (11b) due to the action of the fan (12), which suctions it out of the intake region (11a) and presses it into the first overpressure region (11b).

The bearing element (14) separates the first overpressure region (11b) from the second overpressure region (11c) and implements a positive guide of the air from the first overpressure region (11b) into the second overpressure region (11c) in such a way that the air flows along the heat sink (15) and a heat exchange takes place between air and heat sink (15).

Figure 4:
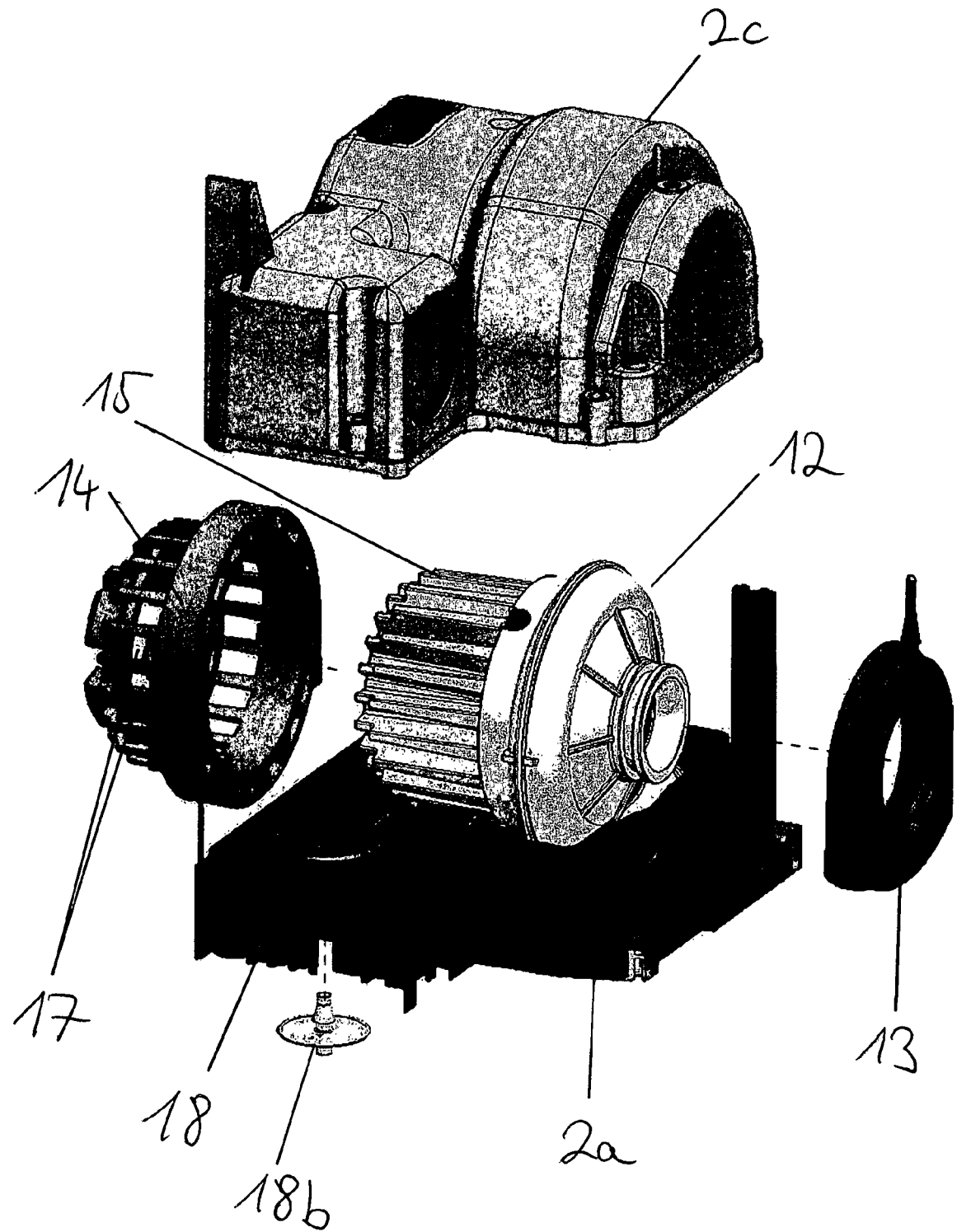
FIG. 4: shows a perspective view of a fan module according to the invention of a device for respiration.

The essential elements for illustrating the guide structures in the region of the fan (12) are shown in perspective in FIG. 4. The fan (12) is connected to the associated heat sink (15). The first bearing element (13), in which the fan can be supported in the region of the intake opening, is shown on the right adjacent to the fan (12). On its inner side, the first bearing element (13) comprises a counter structure adapted to the shape of the fan (12) in the region of the intake opening. On its outer side, the first bearing element (13) comprises a radial peripheral groove, using which the first bearing element (13) is insertable into a corresponding tongue-like counter structure in the housing (2) of the device for respiration (1).

The second bearing element (14), which supports the fan (12) in the region of the heat sink (15), is arranged on the left adjacent to the heat sink (15). On the side facing toward the heat sink (15), the second bearing element (14) comprises a reinforced bead, which is insertable into a corresponding counter structure in the housing (2). Furthermore, the outflow opening (17) of the second bearing element (14) is implemented as an arrangement of multiple smaller openings, which are adapted in the size and position thereof to the structure of the heat sink (15).

A check membrane (18b), which implements the check valve with the cylindrical tubes (18a) and the local structure of the housing lower part (2a), is shown below the portion shown of the housing lower part (2a) in the region of the cooling screen (18), so that air cannot enter the device for respiration (1) in the region of the air outlet (8).

The fan (2) is enclosed by a hood (2c) inside the housing (2) of the device for respiration (1).

Figure 5:
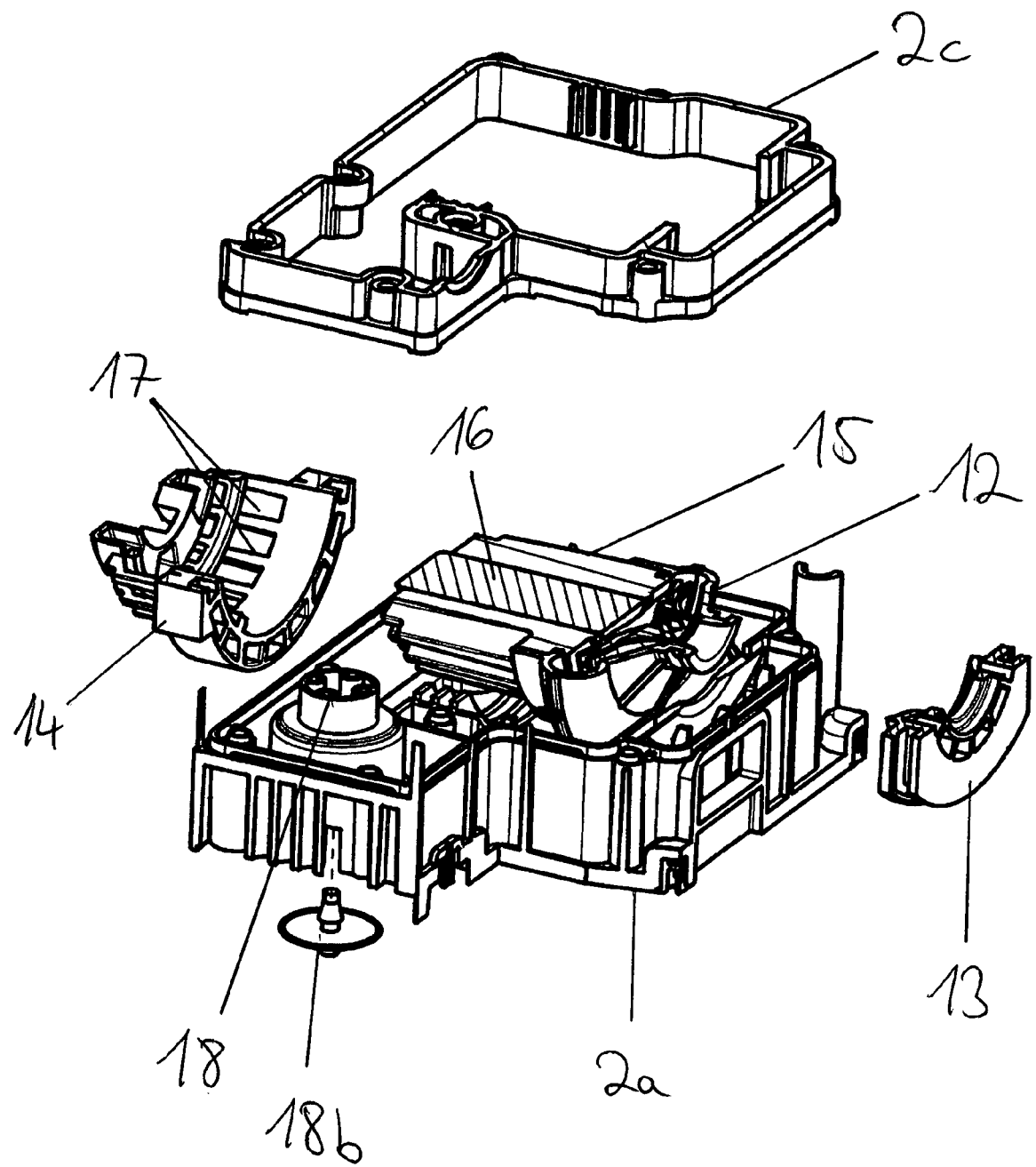
FIG. 5: shows a horizontal section through an exploded illustration of a fan module according to the invention.

FIG. 5 shows a sectional partial view of the elements shown in FIG. 4 of the device according to the invention for respiration (1).

Figure 6:
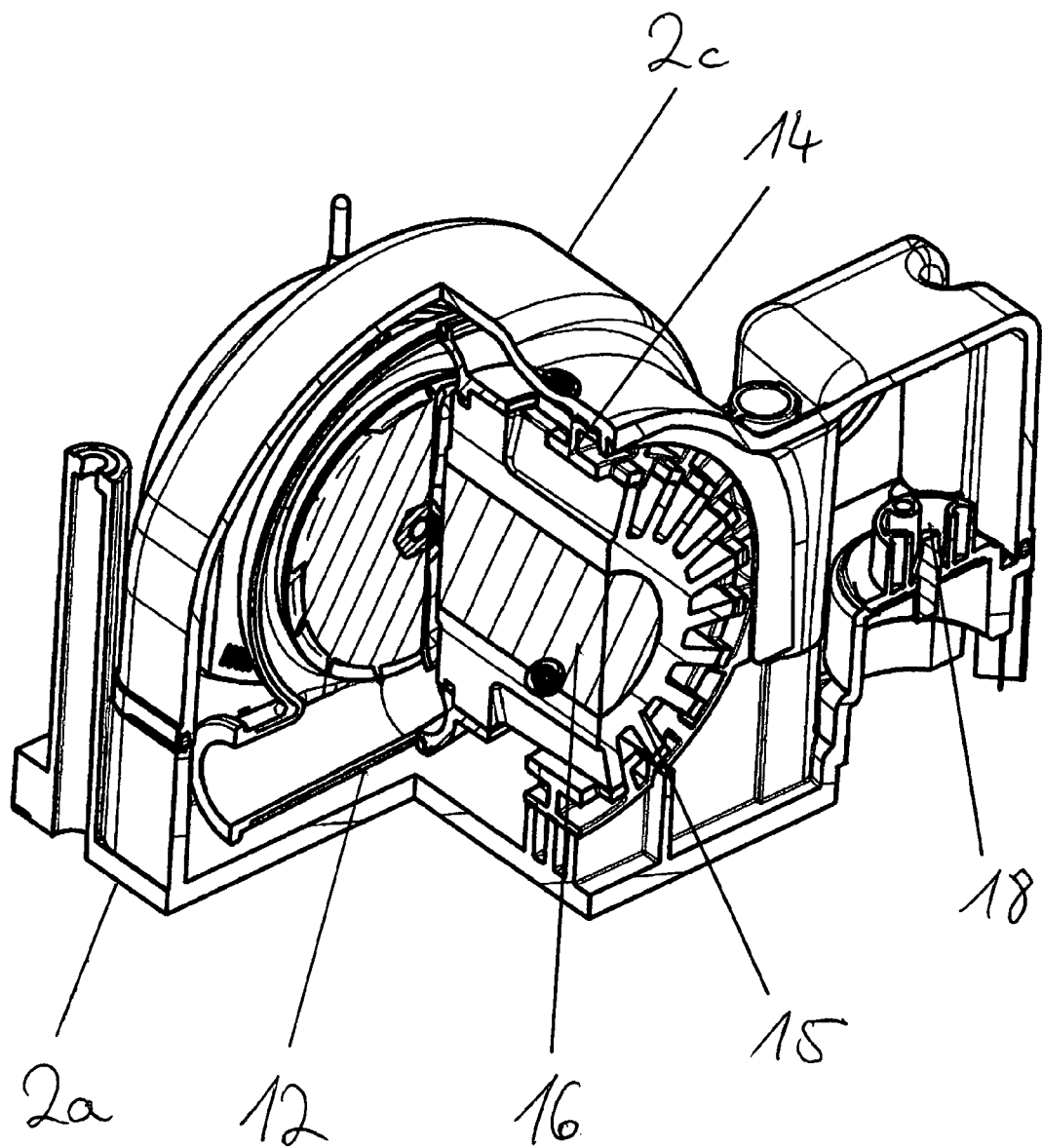
FIG. 6: shows a perspective view with multiple cutaways of a fan module according to the invention of a device for respiration.

A perspective view with multiple cutaways of the elements shown in FIGS. 4 and 5 in the region of the fan (12) of a device according to the invention for respiration is shown in a different viewing angle in FIG. 6.

The invention claimed is:

1. A device for respiration, comprising: a heat sink; a fan; a fan motor that drives the fan; and at least one bearing element, the fan motor being at least partially supported on the at least one bearing element, and wherein the at least one bearing element has a guide structure configured to positively guide cooling air moved by the fan in a region of the heat sink, wherein the at least one bearing element is made of silicone, wherein the guide structure for the cooling air is formed so that the cooling air is guidable in a manner adapted to a structure of the heat sink, and wherein the at least one bearing element is arranged over the heat sink so as to surround the heat sink in a radial direction.

2. The device according to claim 1, wherein the at least one bearing element includes two bearing elements, of which a first bearing element supports the fan on a side of an intake region and a second bearing element supports the fan in the region of the heat sink.

3. The device according to claim 1, comprising a fan module that includes the heat sink, the fan motor, the fan and a fan hood, wherein the fan includes a fan wheel and a fan shaft, wherein the at least one bearing element includes two bearing elements made of silicone, the fan module being supported by the two bearing elements.

4. The device according to claim 2, wherein at least the second bearing element is configured to slip onto the heat sink and radially peripherally enclose the heat sink at least in regions.

5. The device according to claim 2, wherein at least one of the bearing elements separates and seals off various pressure regions from one another.

6. The device according to claim 1, wherein the device is an emergency respiration device.

7. The device according to claim 6, wherein the device is a mobile emergency respiration device.

8. A method for respiration, comprising the steps of: using a fan in a device for respiration having a heat sink, a fan, and a fan motor, wherein the fan motor is supported on at least one bearing element made of silicone and having a guide structure configured to positively guide cooling air moved by the fan in a region of the heat sink, wherein the guide structure for the cooling air is formed so that the cooling air is guided in a manner adapted to a structure of the heat sink, and wherein the at least one bearing element is arranged over the heat sink so as to surround the heat sink in a radial direction; and permanently blowing out cooling air in a switched-on state of the device for respiration.

9. The method according to claim 8, wherein cooling air is blown out with a permanent volume flow of 25 L/minute to 75 L/minute.

* * * * *